United States Patent
Robbins et al.

(10) Patent No.: US 6,702,765 B2
(45) Date of Patent: Mar. 9, 2004

(54) APPARATUS FOR MEASURING TONGUE/HARD PALATE CONTACT PRESSURE

(75) Inventors: Jo Anne Robbins, Madison, WI (US); Elan D. Bomsztyk, Madison, WI (US); Angela L. Heppner, Madison, WI (US); Christine L. Koranda, New Berlin, WI (US); Aaron R. Kroner, Madison, WI (US); Jon M. Kuchenreuther, New Berlin, WI (US); David M. Meister, Madison, WI (US); Bryan S. Staerkel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 273 days.

(21) Appl. No.: 09/982,633

(22) Filed: Oct. 18, 2001

(65) Prior Publication Data

US 2003/0078521 A1 Apr. 24, 2003

(51) Int. Cl.$^7$ .................. A61B 5/103; G01L 5/00
(52) U.S. Cl. .................. 600/590; 73/379.01
(58) Field of Search .................. 600/587, 590, 600/595; 601/23, 38; 482/8, 10, 11; 340/825.19; 128/857, 858; 73/379.01, 379.02, 379.03

(56) References Cited

U.S. PATENT DOCUMENTS

| | | | |
|---|---|---|---|
| 4,697,601 A | * | 10/1987 | Durkee et al. .............. 600/590 |
| 5,119,831 A | | 6/1992 | Robin et al. |
| 5,212,476 A | * | 5/1993 | Maloney ..................... 600/590 |
| 5,609,161 A | * | 3/1997 | Tura et al. .................. 600/590 |
| 5,689,246 A | * | 11/1997 | Dordick et al. ........ 340/825.19 |
| 5,954,673 A | * | 9/1999 | Staehlin et al. ............. 600/590 |
| 6,511,441 B1 | * | 1/2003 | Wakumoto et al. ......... 600/590 |

OTHER PUBLICATIONS

Lazarus, Cathy L., et al., Swallowing and Tongue Function Following Treatment for Oral and Oropharyngeal Cancer, Journal of Speech, Language, and Hearing Research, V. 43,1011–1023, Aug. 2000.

Bu Sha, B.F., et al., Force Production of the Genioglossus as a Function of Muscle Length in Normal Humans, J. Appl. Physiol., 88:1678–1684, 2000.

Force Production of the Genioglossus as a Function of Muscle Length in Normal Humans by B.F. Sha, et al., Journal of Applied Physiology, 88, (5), 1678–84.

Swallowing and Tongue Function Following Treatment for Oral and Oropharyngeal Cancer, by Lazarus, et al., 2000, Journal of Speech, Language and Hearing Research 43 1011.

* cited by examiner

Primary Examiner—Eric F. Winakur
(74) Attorney, Agent, or Firm—Quarles & Brady LLP

(57) ABSTRACT

A mouth supported tongue/hard palate pressure sensor allows pressures to be measured between the tongue and hard palate in an environment that closely approximates the configuration of the tongue and mouth during natural swallowing to provide diagnosis and therapy for swallowing disorders.

26 Claims, 3 Drawing Sheets

APPARATUS FOR MEASURING TONGUE/HARD PALATE CONTACT PRESSURE

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates generally to a medical instrument for measuring the strength of the tongue, and in particular, to an instrument for measuring contact pressures between the tongue and the hard palate for the diagnosis and treatment of swallowing disorders.

Tongue strength decreases as a person ages. A sufficient loss of tongue strength can lead to swallowing disorders, which in turn can cause physical disease in the individual as well as deprive the individual of the pleasure of eating. Nevertheless, research has shown that exercise of the tongue by pressing it against the hard palate for a number of repetitions each day at a given force level may increase tongue strength and may help improve the swallowing function.

A number of methods exist to measure tongue strength. Qualitatively the clinicians may have a patient press against a tongue depressor with his or her tongue.

The Tongue Force Measurement Systems (TOMS) developed by S. N. Robinovich, et al., provides a more accurate alternative. The TOMS device employs a custom built, dental-putty mouthpiece to align a user's tongue with a cantilevered beam. Force on the beam is detected by strain gauges sensing beam deflection. The TOMS device requires that the patient's mouth be open at about 40% of its maximum limit. A substantial portion of the TOM's mechanism extends outside the patient's mouth and is supported by an adjustable arm.

The National Institutes of Heath also produces a device to measure tongue strength, termed the APLSILT system. This device, which is commercially available from ACW Research Incorporated of Chatham, N.J., uses disposable tongue depressor mounted on a load cell held by a mechanism on an adjustable table. Only the tongue depressor is placed within the patient's mouth with the remaining portions of the mechanism being outside of the patient's mouth and supported on the table.

A Lingual Force Transducer, described in the paper *Force Production of the Genioglossus as a Function of Muscle Length in Normal Humans*, by B. F. Sha, et al. Journal of Applied Physiology, 88, (5), 1678–84, includes a compact housing that may be inserted into the patient's mouth and which exposes a balloon on its leading surface. The balloon is connected to a pressure transducer and the device measures the force exerted by the tip of the tongue pressing in a direction out of the mouth, on the balloon.

The Iowa Oral Performance Instrument (IOPI), described in the article *Swallowing And Tongue Function Following Treatment For Oral And Oropharyngeal Cancer*, by Lazarus, et al. 2000, Journal of Speech, Language and Hearing Research 43, 1011, is an air filled bulb, freely moveable within the mouth and attached to a hose that may be connected to a pressure transducer outside of the mouth. The transducer provides a light emitting diode display that indicates pressure on the bulb as a proportion of a manually set maximum to provide visual feedback to motivate the patient in an exercise program.

BRIEF SUMMARY OF THE INVENTION

The present invention provides a device that allows placement of thin pressure sensors adjacent to the hard palate to measure tongue strength in an environment that closely matches the environment of normal swallowing, particularly with respect to mouth opening and tongue placement. The present invention also provides an in-mouth system that aligns itself against other mouth structure for repeatable and accurate measurements over the course of a diagnosis or exercise program. Thus, the invention is usable both by patients and healthy individuals who can be helped by an exercise program (henceforth collectively: "clients").

Specifically, then, the present invention provides an apparatus for measuring the pressure exerted by a client's tongue against the hard palate. The invention includes a sensor support surface sized to fit closely adjacent to the hard palate and a mouth registration means attached to the sensor support and engaging the mouth structure to reproducibly locate the sensor support within the client's mouth. At least one electronic pressure sensor is positioned on a lower surface of the sensor support wholly within the mouth and facing the tongue to be activated thereby; and, an electronic annunciator communicates with the electronic pressure sensor to provide an indication to the client of the pressure measured by the electronic pressure sensor upon pressure by the tongue.

Thus, it is one object of the invention to provide a sensor system that allows the tongue pressure to be measured with the tongue positioned adjacent to the hard palate as during swallowing and that further allows the mouth to be closed to better approximate the natural mouth position during swallowing.

It is another object of the invention to provide these benefits in a system that presents an indication to the client for encouragement and feedback during training exercises.

Two electronic pressure sensors may be positioned on the lower surface of the support displaced along a midsagittal plane.

Thus, it is another object of the invention to provide finer resolution of measurement to the pressures between the tongue and hard palate such as may provide better insight of the swallowing process for a particular client.

The mouth registration means may include at least one surface engaging the client's teeth, for example, like the structure of a dental retainer, or as an interdental plate fitting between the client's teeth to be clamped thereby, allowing substantially full closure of the client's mouth for swallowing.

Thus it is another object of the invention to provide a simple registration means for the pressure sensors, such as allows reproducible measurement of tongue/hard palate pressures without the need for extensive mechanisms that must be independently supported or that limit the positioning of the client's head.

The mouth registration means may include either additionally or alternatively at least one surface engaging the client's hard palate, for example, a conformal mold of the client's hard palate.

Thus, it is another object of the invention to provide a registration means that helps to support the forces of tongue/hard palate interaction and that promotes accurate registration at the points of pressure measurement.

When the mouth registration surface is an interdental plate, it may be C-shaped and the sensor support may be a cantilevered arm attached to a point centered on the C of the interdental plate to extend upward from a plane of the C in the direction of curvature of the C.

It is thus another object of the invention to provide a simple structure for the support of the pressure sensors that may be readily adapted to a variety of different mouth sizes. The interdental plate may be a standard heat moldable mouthguard adjustable to conform to the client's teeth and the cantilevered arm may be adjustable through either bending or replacement to provide the proper depth and height for the client's mouth.

The electronic annunciator may communicate via conductive cables with the electronic pressure sensor where the cables include a connector for releasably separating the conductive cables into two portions. As mentioned, the sensor support may be removable from the mouth registration means.

Thus, it is another object of the invention to provide a sensor system that may be disassembled for easy cleaning of the mouth contacting parts.

The annunciator may be selected from the group consisting of a lamp, a tone generator, and a digital display. The digital display may provide a display of peak pressure, average pressure, or percentage of a predetermined peak pressure.

Thus is therefore another object of the invention to provide flexibility in communication of the pressure data to the client or the clinician according to the demands of different applications.

The annunciator may provide an indication of a pressure exceeding a predetermined threshold. In one embodiment, the predetermined threshold may be increased according to a predetermined schedule.

Thus, it is one object of the invention to provide a pressure sensing apparatus suitable for use in therapy in which a client is encouraged to provide a given pressure to the apparatus and that pressure is regularly increased in a training regime.

The foregoing objects and advantages may not apply to all embodiments of the invention and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
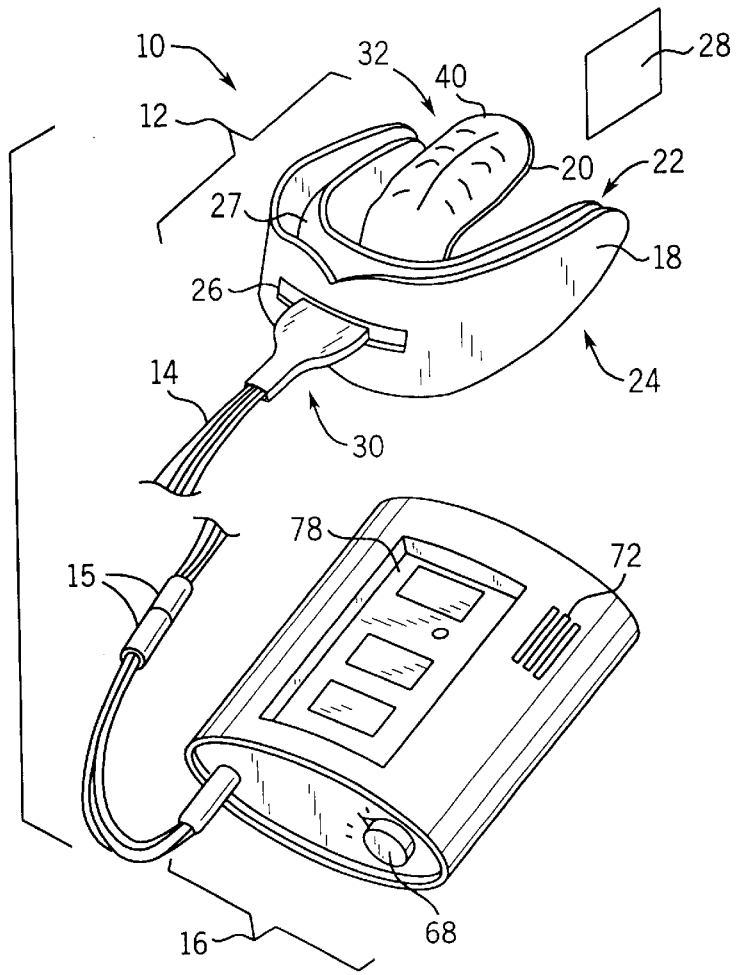
FIG. 1 is a perspective view of the present invention including a mouth-supported portion as attached by cabling to an external annunciator unit.

Referring to FIG. 1, the tongue/hard palate pressure sensor 10 of the present invention includes a mouth-supported portion 12 connected by electrical cable 14 to an external annunciator unit 16. The mouth supported portion 12 includes a mouth registration structure 18 and a sensor support strip 20 both which may fit within a client's mouth when the client's mouth is substantially closed.

The mouth registration structure 18 conforms to the shape of a double mouth guard of a type used for the protection of teeth during athletic activity. Specifically, the mouth registration structure 18 provides for an upwardly opening top channel 22 and downwardly opening bottom channel 24 sharing a C-shaped interdental plate 27, the latter which may be clamped between the client's teeth so that the top channel 22 may engage the upper teeth of the client and the bottom channel 24 may engage the lower teeth of the client. When in use, the C-shaped interdental plate 27 lies within a plane defined by the interface between opposed upper and lower teeth and curves backward along, and symmetrically about, the client's midsagittal plane 28. The mouth guard may be the type manufactured by Everlast Worldwide, Inc of New York, N.Y. under the trade name of Everlast Double Mouthguard.

Figure 2:
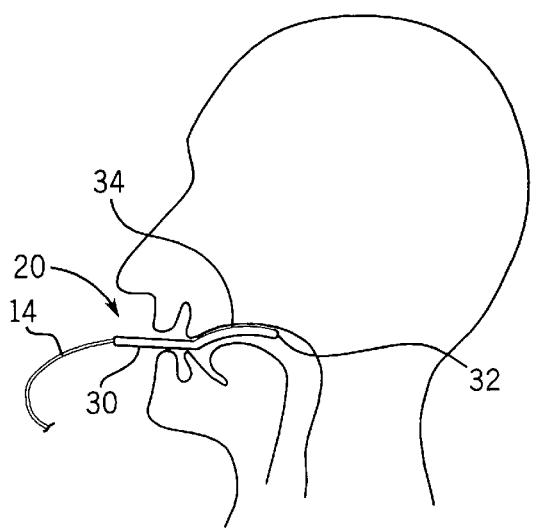
FIG. 2 is a midsagittal cross-section of a mouth cavity showing positioning of a sensor support of the mouth-supported portion of FIG. 1 within a client's mouth.

Referring also to FIG. 2, through the apex or front most portion of the C-shaped interdental plate 27, a rectangular slot 26 may pass, providing an opening extending between the channels 22 and 24. The sensor support strip 20 may extend rearward along the midsagittal plane 28 through the rectangular slot 26 and affixed to the mouth registration structure 18 at the rectangular slot 26. A shank portion 30 of the sensor support strip 20 may connect to the electrical cable 14 pass between the client's incisors when the client's mouth is closed. A spoon portion 32 of the sensor support strip 20 may continue rearward into the client's mouth and upward to closely conform to the client's hard palate 34. The sensor support strip 20 is thus attached in cantilevered fashion to the mouth registration structure 18 to be independently adjustable.

Figure 3:
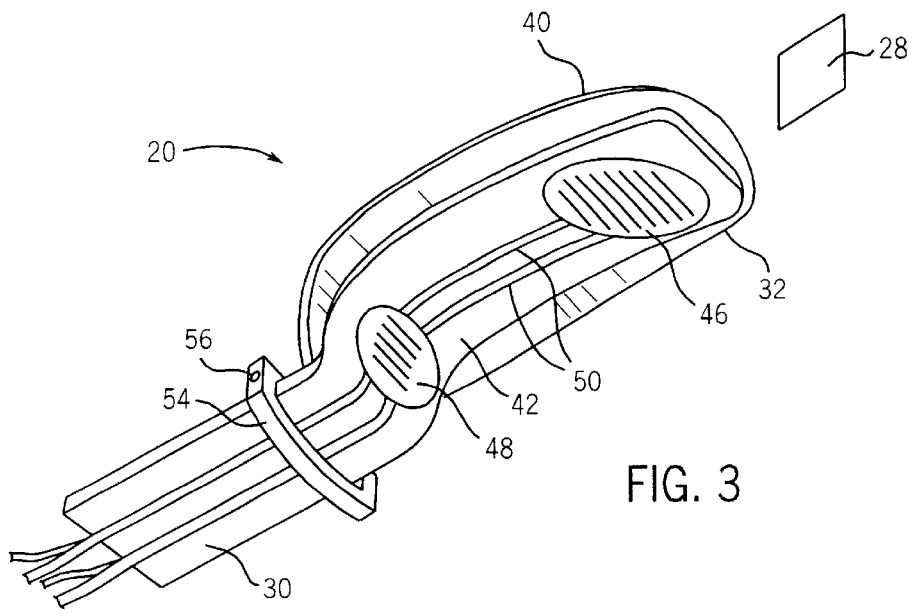
FIG. 3 is a perspective view from below of the sensor support of FIG. 2 showing location of the sensors and the retaining collar that may releasably engage a mouth registration means.

Referring now to FIGS. 1 and 3, the upper surface of the sensor support strip 20 includes a molded structure 40 conforming to the hard palate 34 to be well supported by the hard palate 34 and to provide additional registration for the sensor support strip 20. The molded structure 40 may be fashioned from a cold cure dental acrylic of a type well known in the art.

Underlying the molded structure 40 is a stainless steel strip 42, which may be wrapped with polyolefin heat shrink tubing (not shown). The molded structure 40 may be attached to the polyolefin on the top of the stainless steel strip 42 and two pressure sensors 46 and 48 may be attached directly to the underside of the spoon portion 32 of the stainless steel strip 42 using a thin film of silicone rubber adhesive (not shown). The pressure sensors 48 and 46 may be displaced along the midsagittal plane 28 to provide two points of measurement of tongue pressure, one near the front of the hard palate 34 and one near its center. The connecting wires 50 of the sensors 46 and 48 may be run along the underside of the stainless steel strip 42 toward the shank portion 30 and the front of the mouth and are, with the sensors 46 and 48, ultimately covered with the heat shrink tubing.

Referring to FIGS. 1 and 3, the sensor support strip 20 may be attached to the rectangular slot 26 by means of a cold cured dental acrylic. Alternatively, the shank portion 30 of the sensor support strip 20 may include a molded collar 54 having detent 56 that releasably engage with complementary detent structure in the rectangular slot 26 to allow removal of the sensor support strip 20 from the rectangular slot 26 and thus from the mouth registration structure 18. This simplifies cleaning and repair of the device and further allows the mixing of different standard sizes of sensor support strips 20 and mouth registration structures 18 to match different clients. The collar 54 may be designed to work with off the shelf double mouth guards, thus lowering the total cost of the device.

For the purpose of cleaning and storage, the electrical cable 14 may be broken by electrical connector 15 allowing it to be disconnected from the annunciator unit 16. This also allows one annunciator unit 16 to be shared with multiple mouth-supported portions 12.

Figure 4:
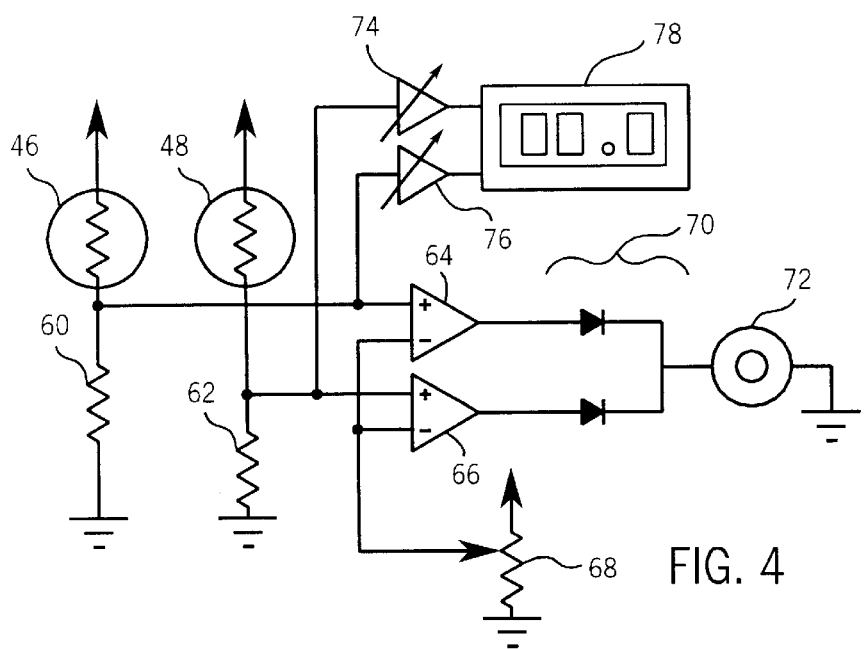
FIG. 4 is an electrical schematic of the sensors of FIG. 3 as attached to circuitry of the external annunciator unit for providing audible and visual feedback to the client.

Referring now to FIGS. 1 and 4, each of the pressure sensors 46 and 48 may be conductive, thick-film polymer sensors of a type commercially available under the tradename: FSR® Model 400 from Interlink Electronics of Camarillo, Calif. providing a change in electrical resistance under pressure as detected by interdigitated electrodes on one or both surfaces of a flat polymer disk. Alternative pressure sensors including those based on strain gauges, piezoelectric materials or mechanical switches may also be used.

Pressure sensors 46 and 48 are connected within the annunciator unit 16 to provide the upper leg of two resistive ladders, with pressure sensor 46 being in series with resistor 60 and sensor 48 being in series with resistor 62. Resistors 60 and 62 are selected to provide the maximum dynamic range of voltage change at the junction of the resistance and the sensor consistent with the desired power dissipation. The upper and lower terminals of the resistive ladders are connected across a source of DC power supplied from a nine-volt battery (not shown).

The junction of resistor 60 and pressure sensor 46 is attached to the non-inverting input of operational amplifier 64 and the junction of resistor 62 and sensor 48 is attached to the non-inverting input of operational amplifier 66. The inverting inputs of operational amplifiers of 64 and 66 are attached to a center tap of a potentiometer 68 whose other terminals are attached across the local voltage source. The operational amplifiers 64 and 66 are operated in open loop configuration to provide voltage comparators whose comparison threshold is determined by the potentiometer 68. The control of the potentiometer 68 may be accessible to the client or clinician so that it may be adjusted to set the threshold of pressure required for the outputs of the operational amplifiers 64 and 66 to provide a high state voltage.

The outputs of the operational amplifier 64 and 66 are connected through an OR-gate formed by two diodes 70 to an audio transducer 72 to provide an audible indication when the set threshold pressure has been achieved or exceeded at either of pressure sensors 46 and 48.

Alternatively, but not shown, two audio transducers 72 may be used having slightly different tones and attached individually to the outputs of operational amplifiers 64 and 66 to provide an indication both that the pressure has been exceeded and the location of the pressure.

Alternatively, the audio transducers 72 may be replaced or supplemented with a visual transducer such as an LED or other visual system.

The junction of resistor 60 and pressure sensor 46 may also be attached to a variable gain amplifier 74 while the junction of resistor 62 and sensor 48 may also be attached to variable gain amplifier 76, each of whose outputs go to a multiplexed digital display 78 which provide a quantitative output indicating actual pressure applied to the pressure sensors 46 and 48. The variability of the variable gain amplifiers 74 and 76 allows calibration of the digital display 78 so as to read in convenient units of pressure or arbitrary normalized units suitable for this purpose.

Alternatively, but not shown, two displays 78 may be used, one connected to each of the outputs of variable gain amplifier 74 and 76. Digital displays 78 of this type are readily available from a number of commercial sources and include internal analog to digital converter and the necessary character generation circuitry.

The digital display 78 may work in conjunction with the audio transducer 72 to provide setting of the potentiometer 68. A series of exercises may be performed by the client pressing upward against the sensors 46 and 48 with the client or clinician observing the digital display 78. The potentiometer 68 may then be set to a desired training level based on observation of the digital display 78.

Figure 5:
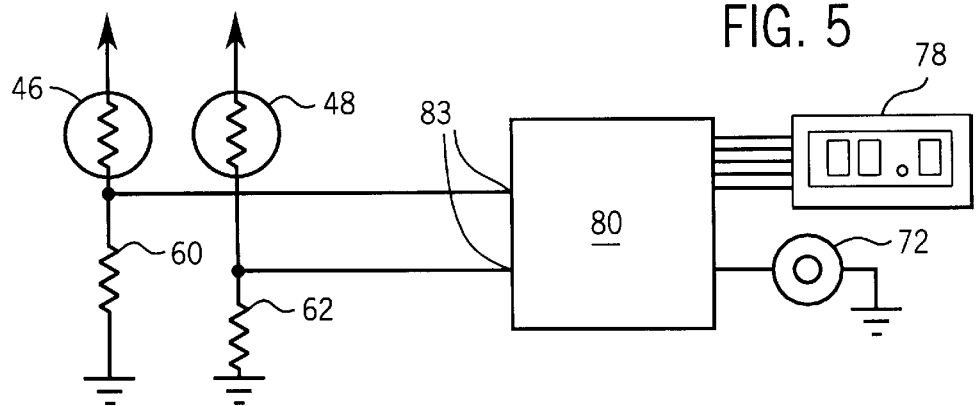
FIG. 5 is an alternative schematic showing the sensors attached to a microcontroller within the external annunciator unit.

Referring now to FIG. 5, it will be understood to those of ordinary skill in the art that the circuitry of FIG. 4 may be implemented in a variety of different ways using techniques well known in the art. One such embodiment may include the use of a microcontroller 80 having analog inputs 83 communicating with internal analog to digital converters for connecting directly to the junctions of pressure sensors 46 and resistor 60 and sensor 48 and resistor 62, respectively. The microcontroller 80 may directly control the digital display 78 through binary output lines as well as with the audio transducer 72. Such microcontrollers 80 are manufactured by the Microchip company of Chandler, Ariz.

Figure 6:
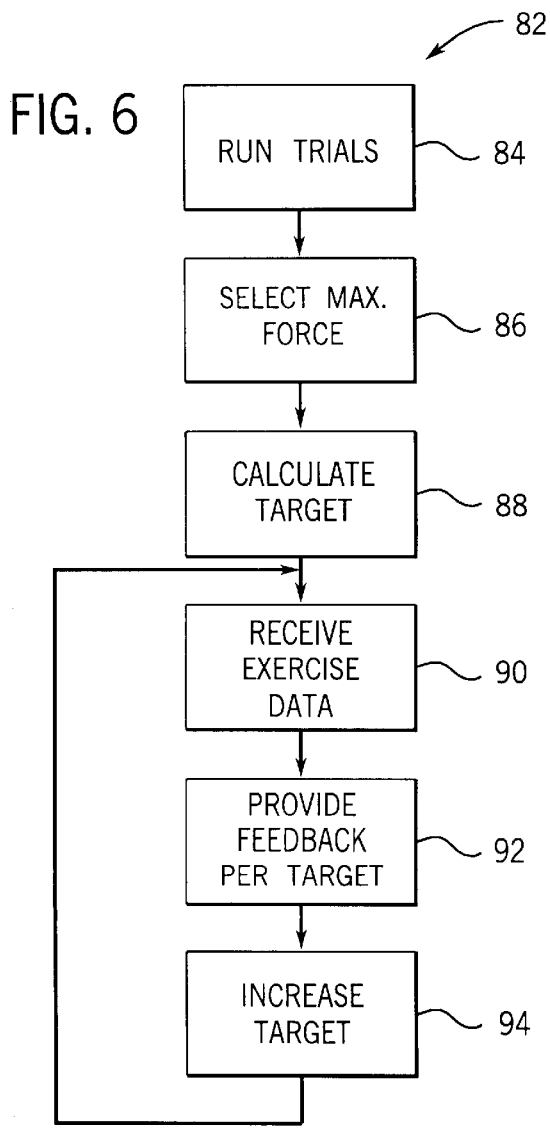
FIG. 6 is a flow chart of the program of the microcontroller such as may provide an exercise regime to a client for improving tongue strength.

Referring to FIG. 6, the microcontroller 80 may be programmed to execute a program 82 providing additional functions to the above device. At a first process block 84 of the program 82, the microcontroller 80 receives data from the pressure sensors 46 and 48 for a series of trials during which the client presses upward with the tongue, toward the hard palate 34 to exert a peak pressure. The peak pressure may be simultaneously shown on digital display 78.

At process block 84, the peak pressure for each of these trials is stored in the on-board memory of the microcontroller 80 and at process block 86, a maximum one of these pressures is selected.

At process block 88, the maximum pressure is reduced by a predetermined percentage, preferably 80%, to become a pressure amount for subsequent exercises by the client.

At process block 90, during a subsequent exercise session by the client, the microcontroller 80 receives new pressure data from the pressure sensors 46 and 48 and at process block 92, the microcontroller provides feedback in the form of an audio signal through audio transducer 72 to the client when the target amount has been exceeded. At the same time, the microcontroller 80 may display a percentage of the target amount that has been achieved.

Upon the conclusion of the training session, as indicated by process block 94, the target pressure is increased slightly for the next training session. Over many training sessions, the target pressure is increased to the maximum pressure.

The arithmetic capabilities of the microcontroller 80 allow the display 78 to provide a variety of different modes including display of peak pressure over a predetermined window of time, average pressure over a predetermined window, or percentage of a target pressure as may be desired by process block 92. In addition, the microcontroller 80 may store data for later clinician review. The display 78 may be used to cue the client as to which steps in the exercise program are to be undertaken.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. An apparatus for measuring a pressure exerted by a client's tongue intra-orally comprising:
   a sensor support sized to fit closely adjacent to the palate;
   a mouth registration means attached to the sensor support and adapted to engage structure for reproducibly locating the sensor support within the client's closed mouth, the mouth registration means comprising an interdental plate to which the sensor support is attached as a cantilevered arm;
   at least one electronic pressure sensor positioned on a lower surface of the sensor support and adapted to fit wholly within the mouth and facing the tongue to be activated thereby; and
   an electronic annunciator communicating with the electronic pressure sensor to provide an indication to the client of the pressure measured by the electronic pressure sensor upon pressure by the tongue.

2. The apparatus of claim 1 wherein two electronic pressure sensors are positioned on the lower surface of the sensor support displaced along a midsagittal plane.

3. The apparatus of claim 1 wherein the mouth registration means includes at least one surface adapted to engage the client's teeth or gums.

4. The apparatus of claim 3 wherein the mouth registration means provides a surface adapted to fit between the client's teeth to be clamped thereby allowing substantially full closure of the client's mouth for swallowing.

5. The apparatus of claim 1 wherein the mouth registration means includes at least one surface adapted to engage the client's palate.

6. The apparatus of claim 5 wherein the surface adapted to engage the client's hard palate is a conformal mold of the client's hard palate.

7. The apparatus of claim 1, wherein the interdental plate is C-shaped and wherein the sensor support is attached to a point centered on the C of the interdental plate to extend upward from a plane of the interdental plate in the direction of curvature of the interdental plate.

8. The apparatus of claim 1 wherein the mouth registration means is a thermoplastic material pliable at temperatures below 100 degree Celsius to be heat moldable to conform to the client's mouth.

9. The apparatus of claim 1 wherein the sensor support is removably engageable with the mouth registration means.

10. The apparatus of claim 1 wherein the electronic pressure sensor and the electronic annunciator communicated via conductive cables and including a connector for releasably separating the conductive cables into two portions.

11. The apparatus of claim 1 wherein the pressure sensor is selected from the group consisting of a mechanical switch, a piezoelectric pressure sensor and a conductive polymer pressure sensor.

12. The apparatus of claim 1 wherein the electronic annunciator is selected from the group consisting of a lamp, a tone generator, and a digital display.

13. The apparatus of claim 1 wherein the electronic annunciator is a digital display providing a display selected from the group consisting of peak pressure, average pressure, and percentage of a predetermined target pressure.

14. The apparatus of claim 1 wherein the electronic annunciator provides an indication of a pressure exceeding a predetermined threshold.

15. The apparatus of claim 14 wherein the predetermined threshold is increased according to a predetermined schedule.

16. The apparatus of claim 1 including a memory means communicating with the electronic pressure sensor for storing values therefrom.

17. A method of strengthening tongue function comprising the steps of:
   (a) positioning a pressure sensor within the mouth of a client, the pressure sensor having a sensor support sized to fit closely adjacent to the hard palate, a mouth registration means attached to the sensor support and adapted to engage mouth structure to reproducibly locate the sensor support within the client's mouth, at least one electronic pressure sensor positioned on a lower surface of the sensor support and adapted to face the tongue to be activated thereby; and an electronic annunciator communicating with the electronic pressure sensor to provide an indication to the client of the pressure measured by the electronic pressure sensor upon pressure by the tongue;
   (b) causing the client to press upward on the electronic pressure sensor with the client's tongue at least once to establish a maximum tongue pressure;
   (c) adjusting the electronic annunciator to provide an indication to the client when a training pressure of the tongue against the electronic pressure sensor has been achieved, where the training pressure is a predetermined fraction of the maximum tongue pressure; and
   (d) gradually increasing the training pressure.

18. The method as defined in claim 17, wherein step (d) comprises the step of increasing the selected training pressure each time the apparatus is used in a training session.

19. The method as defined in claim 17, wherein step (b) further comprises causing the client to press upward on the electronic pressure sensor with the client's tongue a series of times to establish a maximum tongue pressure, and establishing an initial training pressure as a percentage of the maximum tongue pressure.

20. The method as defined in claim 19, further comprising the step of displaying at least one of a peak pressure, an average pressure, or a percentage of the training pressure.

21. The method as defined in claim 17, wherein step (d) comprises increasing the training pressure at the end of each of a plurality of training sessions until the training pressure reaches the maximum tongue pressure.

22. An apparatus for strengthening tongue pressure intra-orally comprising:
   a sensor support sized to fit closely adjacent to the palate;
   a mouth registration means attached to the sensor support and adapted to engage mouth structure to reproducibly locate the sensor support within the client's closed mouth;
   at least one electronic pressure sensor positioned on a lower surface of the sensor support and adapted to fit wholly within the mouth and facing the tongue to be activated thereby; and
   an electronic annunciator communicating with the electronic pressure sensor to provide an indication to the client when a pressure exerted on the pressure sensor exceeds a selected target pressure.

23. The apparatus as defined in claim 12, further comprising a processing unit coupled to the electronic pressure sensor to receive a pressure signal from the electronic pressure sensor and to the electronic annunciator to provide a command signal to activate the annunciator.

24. The apparatus as defined in claim 23, wherein the processing unit is programmed to select the target pressure as a function of a percentage of a maximum pressure produced by the patient during a trial.

25. The apparatus as defined in claim 23, wherein the processing unit is programmed to increase the selected target pressure as the apparatus is used.

26. The apparatus as defined in claim 23, further comprising a display coupled to receive a signal from the processing unit and to selectively display at least one of a peak pressure, an average pressure, and a percentage of the target pressure.

* * * * *

UNITED STATES PATENT AND TRADEMARK OFFICE
CERTIFICATE OF CORRECTION

PATENT NO. : 6,702,765 B2
DATED : March 9, 2004
INVENTOR(S) : Jo Anne Robbins et al.

It is certified that error appears in the above-identified patent and that said Letters Patent is hereby corrected as shown below:

<u>Title page</u>,
Item [75], Inventors, "David M. Meister" should be -- David W. Meister --.

Signed and Sealed this

Twenty-seventh Day of July, 2004

JON W. DUDAS
*Acting Director of the United States Patent and Trademark Office*